(12) United States Patent
Gillbe et al.

(10) Patent No.: US 9,597,520 B2
(45) Date of Patent: Mar. 21, 2017

(54) ELECTRICAL STIMULATION OF THE CAROTID ARTERY

(71) Applicant: Bioinduction Limited, Bristol, Avon (GB)

(72) Inventors: Ivor Gillbe, Bristol (GB); Nikunj K. Patel, Bristol (GB)

(73) Assignee: Bioinduction Limited, Bristol (GB)

( * ) Notice: Subject to any disclaimer, the term of this patent is extended or adjusted under 35 U.S.C. 154(b) by 0 days.

(21) Appl. No.: 14/403,841

(22) PCT Filed: May 24, 2013

(86) PCT No.: PCT/GB2013/051378
§ 371 (c)(1),
(2) Date: Nov. 25, 2014

(87) PCT Pub. No.: WO2013/179006
PCT Pub. Date: Dec. 5, 2013

(65) Prior Publication Data
US 2015/0112359 A1    Apr. 23, 2015

(30) Foreign Application Priority Data
Jun. 1, 2012   (GB) .................................. 1209771.3

(51) Int. Cl.
| A61N 1/00 | (2006.01) |
| A61N 1/378 | (2006.01) |
| A61N 1/05 | (2006.01) |
| A61N 1/36 | (2006.01) |
| A61N 1/372 | (2006.01) |

(52) U.S. Cl.
CPC ......... *A61N 1/3787* (2013.01); *A61N 1/0551* (2013.01); *A61N 1/0558* (2013.01); *A61N 1/3611* (2013.01); *A61N 1/36117* (2013.01); *A61N 1/36125* (2013.01); *A61N 1/37223* (2013.01)

(58) Field of Classification Search
USPC ...................................................... 607/2, 118
See application file for complete search history.

(56) References Cited

U.S. PATENT DOCUMENTS

| 5,983,141 A | 11/1999 | Sluijter et al. |
| 2001/0003799 A1 | 6/2001 | Boveja |
| 2004/0010303 A1* | 1/2004 | Bolea ................. A61B 5/02028 607/118 |
| 2007/0239224 A1 | 10/2007 | Bennett et al. |

(Continued)

OTHER PUBLICATIONS

Philippe Lahorte, International Search Report, Aug. 27, 2013, 5 pages, European Patent Office, Munich.

(Continued)

*Primary Examiner* — Nicole F Johnson
(74) *Attorney, Agent, or Firm* — McGarry Bair PC

(57) ABSTRACT

In order to treat hypertension, an implantable receiving device is connected to implantable leads, which are adapted to deliver electrical energy to the carotid body or bodies of the patient. The receiving device is arranged to receive electrical energy from an external generator. The device thus enables the delivery of electrical currents, which modify the function of neural tissue, particularly where repeated treatments are needed or where positioning of a percutaneous needle is difficult.

15 Claims, 8 Drawing Sheets

(56) References Cited

U.S. PATENT DOCUMENTS

2009/0143837 A1 6/2009 Rossing et al.
2009/0292335 A1* 11/2009 Leonov ................ H01L 35/30
 607/35
2010/0274219 A1 10/2010 Wenzel et al.
2012/0109250 A1 5/2012 Cates et al.

OTHER PUBLICATIONS

Ingrid Scheffers, Carotid baroreflex activation, a novel method to treat resistant hypertension, 144 pages, Minneapolis, Minnesota, USA. Maastricht University, Maastricht, Netherlands, year 2010.
CVRx Medicine ReEnvisioned, Barostim Neo Legacy Reference Guide—Barostim neo® Legacy system, 43 pages, Minneapolis, Minnesota, Dec. 17, 2014.
Cranial Nerves in Health and Disease, 2002, 2nd edition, Pub: BC Decker Inc, Lead author: Linda Wilson-Pauwels, ISBN: 1-55009-164-6. 1 page containing p. 170, The entire contents are available online here: http://www.slideshare.net/fullscreen/ViralPatel32/cranial-nerves-30632964/1, accessed Aug. 8, 2016.
Haydn Gupwell, Combined Search and Examination Report Under Sections 17 & 18(3), 5 pages, Nov. 19, 2013, Intellectual Property Office, South Wales.

* cited by examiner

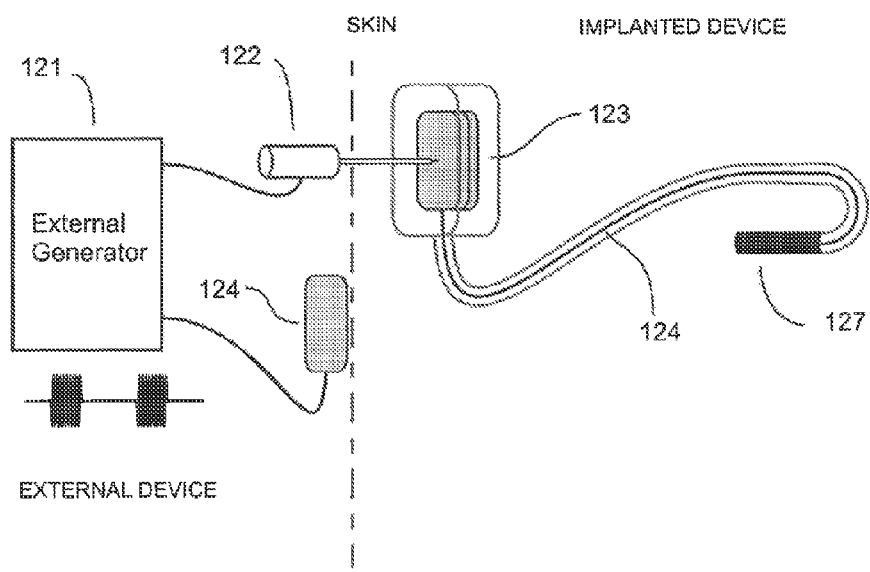
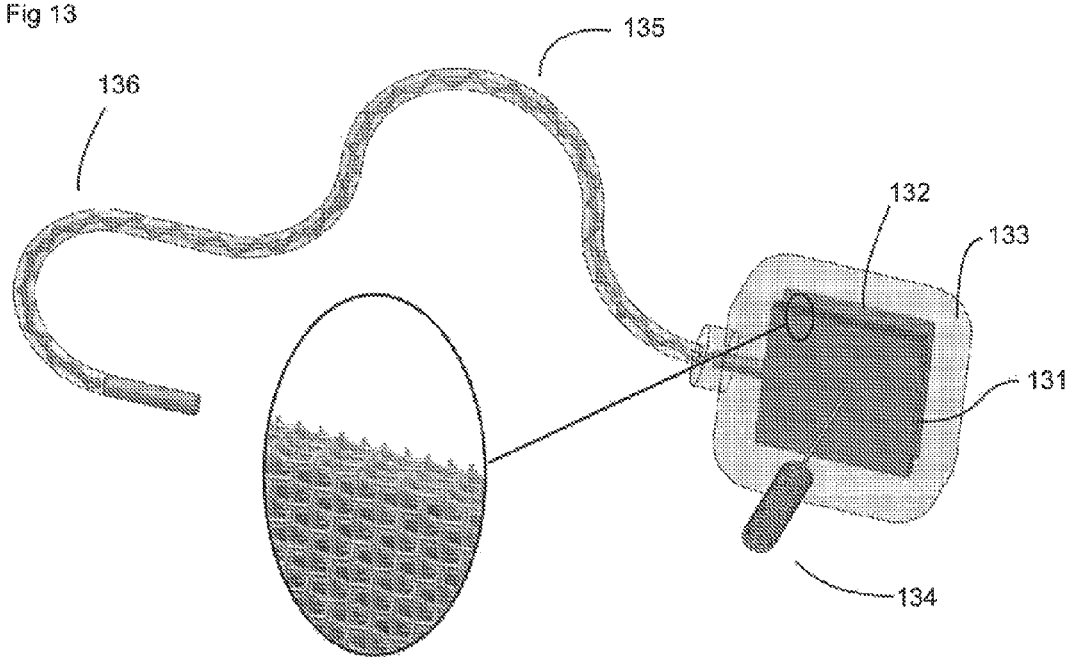

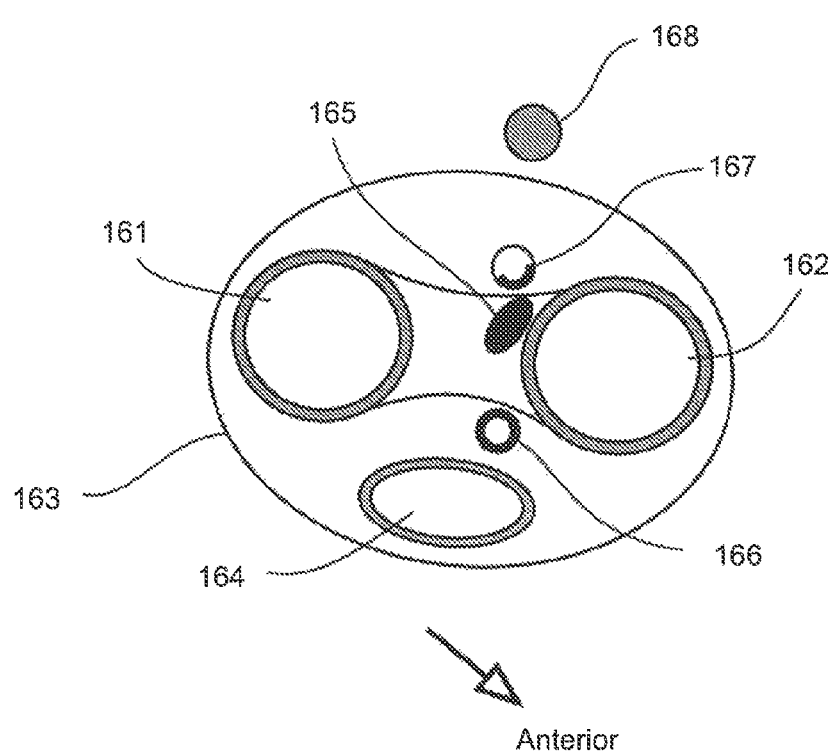

ELECTRICAL STIMULATION OF THE CAROTID ARTERY

CROSS-REFERENCE TO RELATED APPLICATIONS

This application is a National Phase application of International Application No. PCT/GB2013/051378, filed May 24, 2013, which claims the benefit of GB 1209771.3, filed Jun. 1, 2012, both of which are incorporated herein by reference in their entireties.

BACKGROUND TO THE INVENTION

Radiofrequency (RF) thermal ablation has been employed for a number of years as a means of modifying neural tissues, typically as a treatment for pain. The RF signal is delivered using a percutaneous needle with an insulated shaft and exposed tip which is positioned over the target nerves. Temperatures of minimum 60° C. are used to produce long-term pain relief through coagulation of tissue. Control of probe tip temperature is important; typically a temperature sensor at the tip is used so that power delivery can be modulated appropriately. RF devices deliver energy in the form of a sinusoidal waveform at 250 to 500 KHz, well above the range at which nerve fibres will respond. At the frequencies concerned, tissue impedance is typically in the range of 100 to 500 ohm and the peak voltage of the waveform is 60 to 100 V.

Pulsed radiofrequency (pulsed RF) has emerged in recent years. Pulsed RF uses signals which are interrupted so that tissues surrounding the needle tip have time to dissipate heat and the temperature does not exceed 42-43 degrees centigrade, below the point at which tissues are damaged. Pulsed RF is described by Sluijter et al "Method and apparatus for altering neural tissue function" U.S. Pat. No. 5,983,141 and U.S. Pat. No. 6,259,952. Pulsed RF is considered by many to be a safer alternative to RF ablation as the lack of heat generation limits damage to nearby structures.

The effect of pulsed RF and to a lesser extent thermal RF is temporary because the nerves regenerate, typically lasting for a few weeks to several months after which an additional treatment may be required.

Targets for pulsed RF include facet joint arthropathy, failed back surgery syndrome, nerve root compression, neuropathic spinal pain and chronic headache. For example, pulsed RF applied to the occipital nerve using a percutaneous needle as a treatment for cervicogenic headache may prevent attacks for a number of weeks.

In recent years thermal RF has been employed for treatments other than pain control. An example is renal nerve ablation for modification of sympathetic activity as a treatment for hypertension, described by Demarais et al "Methods and apparatus for thermally-induced renal neuromodulation" U.S. Pat. No. 7,617,005. Around one third of the adult population has high blood pressure or essential hypertension, many patients need a combination of 2 or 3 anti-hypertensive drugs of different classes to adequately lower their blood pressure, but in a significant minority even such a combination of drugs is ineffective. Presently there are only a limited range of treatment options available for patients who develop drug resistance.

In response to this unmet need, other targets and methods of modulating blood pressure by electrical stimulation have been developed. Mayberg "Brainstem and cerebellar modulation of cardiovascular response and disease" WO2004069328 describes a method of control of blood pressure employing electrodes in the brainstem. Kieval et al. "Baroreflex modulation to gradually decrease blood pressure" U.S. Pat. No. 8,060,206 B2 describes simulating baroreceptors in the region of the Carotid sinus to control blood pressure.

In order to facilitate delivery of electrical stimulation chronically, or to locations that are difficult to reach with percutaneous needles, various devices that are implantable but employ external power sources have been developed. Gleason etc al "Implantable nerve stimulation device" U.S. Pat. No. 5,094,242 describes an implantable neurostimulation device which receives energy from an external coil via induction and delivers this energy to an implantable receiving coil. Such inductively coupled devices are well suited to neurostimulation applications as the power requirements of such devices are in the region of a few milliwatts. For RF or pulsed RF devices, the peak power requirements during the pulse is typically in the range of 20 W or more, which requires a powerful external coil as transmission efficiency is unlikely to exceed 10%.

Means of delivering electrical energy by direct electrical connection via a percutaneous needle to an implantable device are also described in the prior art. For example, Mantsch el al "Medical Electrode System" US2008/0215126, now U.S. Pat. No. 9,042,998, describe a flexible electrode and catheter connected to an implantable port into which an external needle is introduced percutaneously for delivery of RF and/or drugs into the epidural space. Malaney et al "Implantable electro-acupuncture device" U.S. Pat. No. 6,377,853 describe a device which is intended for nerve stimulation also employing a needle and implantable port. In both examples, a cone is employed to guide the needle into a contact port so that errors in alignment of the implantable connector and percutaneous needle can be compensated.

SUMMARY OF THE INVENTION

Broadly, the present invention concerns an active implantable device for modifying the function of neural tissue by delivering electrical currents to tissues, in particular where repeated treatments are required, or where intervening or nearby structures may make positioning of a percutaneous needle difficult. The invention uses an implantable receiving device, implantable lead and external generator. The implantable receiving device comprises a means of receiving electrical energy from the external generator, in particular RF energy, either by induction or direct electrical connection using a percutaneous needle. The implantable lead comprises at its proximal end a connector which mates with the implantable receiving device and insulated wires to deliver the electrical energy to one or more contacts at the distal tip of the implantable lead.

In one aspect the invention provides a device for treatment of hypertension, asthma or chronic obstructive pulmonary disease by supplying electrical energy to the carotid body or bodies. The device comprises an implantable receiving device, one or more implantable leads and a generator. In use, the receiving device and leads are implanted. The implantable receiving device receives electrical energy from the external generator and is connected to the implantable lead(s), and each implantable lead is adapted to deliver electrical energy to the carotid bodies by means of one or more electrodes at its distal end.

Preferably the distal end of at least one said implantable lead incorporates an arcuate, e.g. semi-circular, hook that allows the lead to sit over the bifurcation of the internal and external carotid. The hook may incorporate one electrode connected by an insulated wire to the implantable receiving device such that, in use, the electrode is held in close proximity to the carotid body; and in which the electrode is adapted to deliver electrical energy to the carotid body with the electrical return path provided by an electrode local to the implantable receiving device.

Alternatively, the hook may incorporate two electrodes, one on each side of the hook, connected by insulated wires to the implantable receiving device such that, in use, the electrodes are positioned each side of the bifurcation and thereby electrical energy delivered across the electrodes tends to flow through the region of the carotid body.

Preferably, the distal electrode is arranged so that its surface in electrical contact with the tissues covers only the sector of the lead circumference that faces towards the carotid body, typically a 90, 120 or 180 degree arc with its centre offset towards the external carotid artery, so that electrical energy tends to flow towards the carotid body and away from baroreceptors on the internal carotid artery and also away from the sympathetic chain ganglia, thereby reducing the potential for side-effects.

In an embodiment having an arcuate hook, the arcuate shape is preferably formed by a spring so that the hook can be straightened to allow insertion via a tunneling tool such as a hollow hypodermic needle or guide tube.

The generator is preferably adapted to deliver electrical energy in the form of pulsed radiofrequency signals. These can serve to modify the function of the carotid body or bodies without heating the tissues to a temperature at which they are ablated such that the nerve signals from these bodies are attenuated or eliminated with the effect that average arterial blood pressure is reduced for a period of days, weeks or months.

The implantable receiving device is suitably inductively coupled to the external generator. Thus the generator may have a transmitting coil, and the receiving device may have a receiving coil. A near-infrared light emitting diode (LED) may be used for feedback of the voltage at the receiving coil, with the external transmitting coil having an infrared photo detector on its surface configured to detect the activation of the implanted LED. The feedback may be used to detect the resonance frequency of the internal coil and to control the voltage delivered to the implanted electrodes.

Alternatively, the implantable receiving device may be directly coupled to the external generator in use. Thus it may incorporate an implantable port comprising a contact of conductive wire mesh enclosed in a low modulus silicone outer case and a percutaneous needle with insulated shaft with exposed tip which can be inserted into the implantable port to make electrical contact and connected to the external generator.

The invention can be used in a method of treatment of hypertension asthma or chronic obstructive pulmonary disease by supplying electrical energy to the carotid body or bodies by means of an implantable receiving device, one or more implantable leads and an external generator in which the implantable receiving device receives electrical energy from the external generator and is connected to the implantable leads, in which the implantable lead is adapted to deliver radiofrequency energy from the external generator to modify the function of the carotid body or bodies such that the nerve signals from those bodies are attenuated or eliminated with the effect that average arterial blood pressure is reduced for a period of days, weeks or months following treatment. The method also comprises additional periodic treatments with RF energy, typically every few weeks or months, to maintain average arterial pressure at a reduced level.

The method may include the steps of:
Making a first incision in the upper part of the neck with exposure of the carotid bifurcation and a second incision in the lower part of the neck or upper chest at the site of the implantable receiving device;
Tunneling from the first incision to the second incision, or vice-versa, with a Trocar and guide tube or needle;
Introducing an implantable lead through the guide tube or needle between the site of the first and second incisions, with the distal end of the implantable lead sutured in place overlying the carotid bifurcation in close proximity to the carotid body; and
Connecting the implantable lead to the implantable receiving device, which is inserted in a subcutaneous pocket with the face of the implant preferably less than 10 mm below the surface of the skin.

Typically, the first incision is made on the anterior border of the sternocleidomastoid muscle. In cases where the implantable receiving device is comparatively small, the method may include insertion of the implantable receiving device in the first incision under or adjacent to the sternocleidomastoid muscle, thereby eliminating tunneling and reducing the length of the wire required which is preferable as it will reduce surgical time and may also reduce potential heating effects associated with use of Magnetic Resonance Imaging devices.

One type of embodiment is a device for use in a method for treatment of hypertension, asthma or chronic obstructive pulmonary disease comprising an implantable receiving device, one or more implantable leads, and an external generator. The implantable receiving device receives electrical energy from the external generator, is implanted typically 5-10 mm under the skin and is connected to the implantable lead(s). The implantable lead at its proximal end has a connector with one or more insulated wires connected to electrodes at the distal end which are implanted in close proximity to the carotid bodies. The distal end of the lead is adapted to prevent migration from the target by incorporating a semi-circular hook that allows the lead to sit over the bifurcation of the internal and external carotid. Preferably, the hook is formed from an elastic material so that it is possible to introduce the lead down a needle. The method comprises implantation of the lead using a hollow hypodermic needle such as a Tuohy needle or a Trocar and guide tube. The method further comprises periodic delivery of RF energy from the external generator to modify the function of the carotid bodies such that the nerve signals from those bodies are attenuated or eliminated with the effect that average arterial blood pressure is reduced for a period of days, weeks or months following treatment. The method also comprises additional periodic treatments with RF energy, typically every few weeks or months, to maintain average arterial pressure at a reduced level.

Historically, carotid body resection has been employed as a treatment in thousands of patients for asthma and chronic obstructive pulmonary disease. Because of its potential for reduction in sympathetic outflow, it is likely that this may also be a useful intervention for sleep apnea syndrome and diabetes.

Regulation of arterial pressure is not fully understood, but certain mechanisms have been characterised. Two mechanisms of relevance to this invention are as follows:

Baroreceptors are nerve endings located in the wall of the aortic arch and the carotid sinus that detect changes in arterial pressure through stretch of the vessel walls. The receptors are stimulated by stretch and the firing rate increases with pressure. Below a mean pressure of about 60 mmHg, action potential frequency reaches a minimum; above about 160 mmHg the baroreceptors reach a maximum firing rate such that further increases in pressure do not produce an increase in firing rate. Denervation of the baroreceptors in humans produces a long term increase in mean arterial pressure and increased heart rate. Conversely, stimulation of the baroreceptors using a pulse generator may provide a reduction in blood pressure over the long term.

Peripheral chemoreceptors are cells contained within two small carotid bodies located in the bifurcation of the external carotid arteries and the internal carotid arteries, and also contained in aortic bodies located on the aortic arch. These bodies sense the partial pressure of oxygen ($PO_2$) and carbon dioxide ($PCO_2$) in the blood stream and also sense hydrogen ion concentration (pH). Nerve fibres from the carotid bodies increase their firing rate as the partial pressure of oxygen decreases, partial pressure of carbon dioxide increases or pH increases. Typical normal baseline for arterial $PO_2$ is 95 mm Hg, $PCO_2$ is 40 mm Hg. At a threshold of about 80 mm Hg $PO_2$ receptors start to fire, the rate increasing as $PO_2$ decreases. An increase of $PCO_2$ above normal levels also increases firing rate. The signals from these peripheral chemoreceptors are sent to the cardiorespiratory centres in the medulla oblongata, whereby increase activity results in increased sympathetic outflow to the heart. Removal of the carotid bodies in young spontaneously hypertensive rats has been shown to delay onset of hypertension. Similarly, deactivation of carotid or aortic bodies by means of either thermal or pulsed radiofrequency may be expected to cause a similar effect.

Because of the proximity of baroreceptors and peripheral chemoreceptors and the fact that deactivation of these two types of sensors has an opposing effect on blood pressure it will be appreciated that it is desirable to focus RF energy over the carotid bodies in order to maximize therapeutic outcome in the treatment of hypertension.

It is desirable that the RF energy delivered is of a non-thermal nature, so that ablation and possible long term damage to the nerves or carotid bodies or nearby structures does not occur. In order to avoid tissue damage it is important that the temperature of tissue in the proximity of the electrode tip does not exceed 42 to 43 degrees centigrade. As previously described, pulsed radiofrequency is employed for this purpose; comprising short bursts of electrical energy interspaced by quiet periods to allow any generated heat to be conducted away by the tissues. In prior art devices, a temperature sensor is incorporated in the tip of the needle to ensure that the temperature does not rise appreciably. In a long term implant, biocompatibility considerations dictate the use of known biocompatible materials as a sensor. Such an arrangement is possible with a platinum resistance temperature device (RTD) at the distal tip, but such an arrangement requires four additional wires to the tip, two to carry a known current and two to measure the voltage drop across the Platinum resistor. Additionally the RTD requires sensitive electronics in the implant to measure the small changes in the value of resistance with temperature changes. The temperature sensor may be eliminated by careful selection of the applied voltage and mark-space ratio for the waveform such that for a particular electrode configuration heating can be assumed not to occur even in the absence of temperature feedback.

Therefore, it is desirable for simplicity that the device described herein does not employ a temperature sensor, but that control of the applied voltage to the tip electrode is provided so that the heating effects are known from prior testing and simulation and can be compensated by correct selection of applied voltage and mark-space ratio. Two further aspects of this invention comprise methods for supply of a known controlled voltage to the electrode.

In one type of embodiment, the implantable receiving device comprises an implantable port for receiving a percutaneous needle which is connected to the implantable lead. At its proximal end, the implantable lead may have a connector to allow it to be detachable from the implantable receiving device. The implantable lead has an insulated flexible wire that at its distal end is connected to an exposed tip (electrode) which is intended to be surgically positioned so that it overlies the target. The implantable port comprises a contact of conductive wire mesh of typically four to eight layers enclosed in a low modulus silicone outer case. The percutaneous needle has an insulated shaft with exposed tip. On the other end of the percutaneous needle, external to the body, the needle has an area which is not insulated or a connector to allow electrical connection to an external generator. The exposed tip when inserted into the implantable receiving device penetrates through the mesh and makes electrical contact with the mesh, but by virtue of the silicone enclosure and insulated shaft is not in electrical contact with the tissues surrounding the implantable receiving device. The mesh may be made of any conductive material that is biocompatible, in particular implantable grades of stainless steel, such as Fe-17Cr-14Ni-2.5Mo also known as 316L, certain cobalt nickel molybdenum alloys such as Co-35Ni-20Cr-10Mo (trademarked as MP35N) or platinum iridium alloy such as Pt-10Ir. The mesh is backed by a layer of material through which the needle cannot penetrate, such as thin continuous sheet of metal, a polymer or ceramic. The mesh is connected via the insulated wire to the exposed tip at the distal end that is in electrical contact with the target tissue. An electrical circuit is completed by connecting the external generator to the needle with a return path provided by a grounding pad on the patient's skin. Control of voltage of such an arrangement is provided directly by electronics in the external generator. Prior to delivery of RF energy, the external generator measures total resistance of the circuit comprising needle, implantable lead, tissues and the return path via the grounding pad by applying a known small current and measuring the applied voltage. This is used to verify correct connection of the needle and may also be employed to adjust the applied voltage to ensure that heating does not occur.

In another type of embodiment, the implantable receiving device is coupled to the external generator by induction. The implantable receiving device consists of an implantable receiving coil and associated printed circuit board contained in a sealed enclosure, ideally with a connector for the implantable lead. The implantable receiving coil is connected to two electrodes at the distal end of the implantable lead via insulated flexible wires, the electrodes surgically positioned so that they lie either side of the target. Alternatively, one electrode is situated at the distal end of the flexible wire, with a second electrode proximal to the receiving coil. In this case, the return electrode is physically larger than the distal electrode to provide low impedance contact with the tissues. The alternative in which both electrodes are at the distal end of the flexible wire is preferred as this concentrates the RF energy in the location of the target and results in reduced power requirement because the applied electrical field is greater for a given applied voltage by virtue of the proximity of the two electrodes near the target tissues. Preferably, the electrode(s) are arranged so that they form a hook designed to fit over the bifurcation in the carotid artery. The implanted receiving coil is placed in the subcutaneous tissues, typically in the upper chest at a depth of 5-10 mm or at most 20 mm. RF energy is supplied by induction using an external coil overlying the implanted receiving coil. The external generator has a transmitting coil that is positioned on the skin overlying the implanted receiving coil. In order to maximise energy transfer, the implantable coil has a capacitor in parallel chosen to that it is resonant at the RF frequency, typically 250-500 kHz. The exact resonant frequency will however vary within a small range because of the capacitance of the tissues and component tolerances. Tissue capacitance will tend to move the point of resonance and tissue resistance will tend to flatten the resonance curve (reduce the Q of the circuit). At the start of a treatment, it is important that the frequency of excitation of the external transmitting coil is adjusted to the resonant frequency of the receiving coil. This resonant point is difficult to detect in the primary coil because coupling between internal and external coils is typically very poor. Coupling can be increased by using a magnetic material such as ferrite in the core of the receiving coil, but this is not a preferred option as the presence of magnet material in the implant precludes the use of magnetic resonance imaging devices which is an important diagnostic tool in modern medicine. Therefore, a means of feedback from the implant to the internal coil is important to indicate the resonant frequency at which power transfer is maximised. Additionally, because the efficiency of power transfer between coils varies with coil alignment and implantation depth, a means of feedback of the voltage generated on the internal coil is essential.

According to this invention, a near-infrared light emitting diode (LED) is used for feedback of the voltage at the receiving coil and the external transmitting coil has an infrared photo detector on its surface configured to detect the activation of the implanted LED. Soft tissues have relatively low light absorption in the near infrared spectral regions. Taking into account scatter which dominates in the visible wavelengths and absorption which increases deeper into the infrared, the best window for operation is 850 to 1300 nm. A frequency of around 900 nm is ideal.

The implanted LED is powered by energy from the implanted receiving coil. A tap on the output implanted coil is rectified using a diode bridge. A full bridge is preferred to eliminate unbalanced loading on the coil which might result in a DC offset in the applied signal. A comparator measures the voltage generated by the receiving coil which is used to generate a variable mark-space ratio drive for the LED representative of the measured voltage. The voltage set point during operation is a maximum of 100 V but typically 50 V or less. The circuit is arranged so that there is sufficient energy available to illuminate the LED when power is received by the implanted coil at a level much lower than the set point, typically $\frac{1}{10}^{th}$ of the set point and therefore at a level at which there is no danger of tissue heating. The comparator is preferably arranged to drive the LED so that the mark space ratio is at maximum at low voltage and the mark-space ratio reduces as voltage is increased and that the LED is off for 100% of the time when the receiving coil voltage exceeds 120% of the voltage set point. This arrangement has the benefit that it is fail-safe, because when the LED is off, the output from the external coil is reduced to a known safe level at which no heating can occur, typically $\frac{1}{10}^{th}$ of the typical output at the set-point. A further benefit is that at the operating set-point voltage losses in the current source used to drive the LED are minimised as the LED is mostly in the off state.

When the external transmitting coil is first placed over the implantable coil, the generator outputs a low amplitude RF waveform, sufficient to light the LED at resonance, but insufficient to cause therapeutic effects. The external generator sweeps the transmitting coil frequency across the expected resonance range to detect the frequencies at which the implantable LED lights and at which the mark-space ratio is at a minimum which is indicative of the resonance frequency of the internal coil when coupled to the tissues. The external generator then increases RF amplitude until the LED reaches the appropriate mark-space ratio indicative of the pre-defined voltage set point at which pulsed RF is delivered.

The advantage of the above configuration is that the implantable electronics are extremely simple. However, if other more complex features are required, such as temperature feedback, the LED can be employed as a means of transmitting data using one of many known encoding schemes, in this instance, a small microprocessor in the implant may be employed. Another and simpler alternative is to provide feedback of temperature by modulating the frequency of the variable mark-space ratio signal.

BRIEF DESCRIPTION OF THE DRAWINGS

FIG. 12 is a block diagram of a directly coupled pulse RF device, showing major functional elements.

FIG. 13 is a drawing of a typical embodiment of a directly coupled RF device and percutaneous needle.

FIG. 16 is a schematic representation of a cross section of the implantable lead illustrated in figure fifteen in implanted over the carotid bifurcation.

DESCRIPTION

Figure 1:
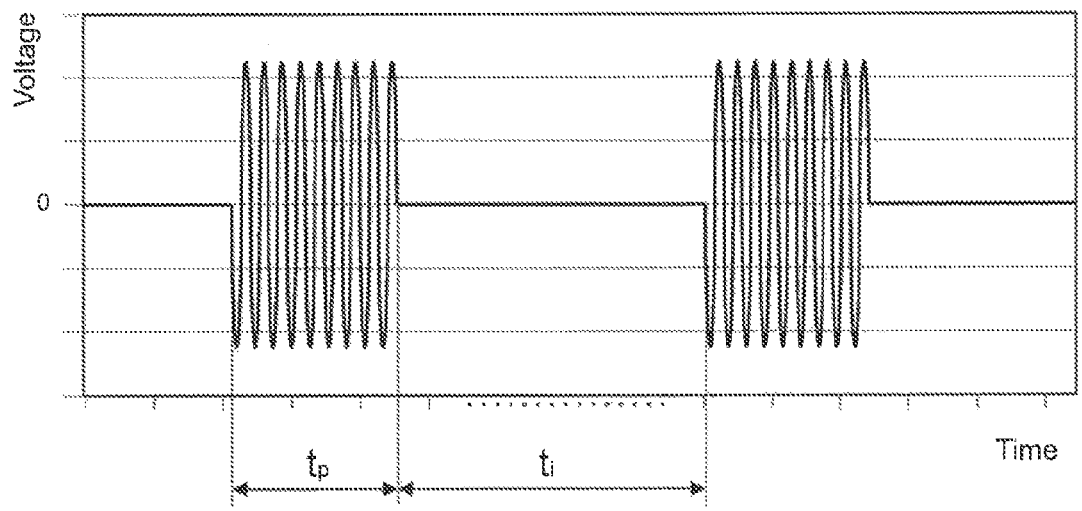
FIG. 1 is an illustration of a typical pulsed RF waveform, in which the horizontal axis is not to scale and number of cycles per pulse has been reduced to enhance readability.

FIG. 1 shows a typical pulsed radio frequency (PRF) waveform, in which the number of cycles in each burst has been reduced for readability and the relative pulse (tp) and space (ti) times are not to scale. In typical applications of open loop pulsed RF in which a temperature sensor is not provided, the pulse time (tp) would be 2 to 10 ms or preferably 5 to 8 ms, each pulse consisting of many cycles of a RF waveform of 200 to 600 kHz, or preferably 250 to 500 kHz. The pulses are repeated at 2 to 8 Hz, preferably at 5 Hz, with a space between each pulse approximately 120 to 500 ms. The voltage amplitude of the waveform would be selected on the basis of testing in simulated or real tissue with the particular electrode combination used so that the tip temperature does not exceed 42 to 43 degrees centigrade during treatment. Typically a peak voltage of 25 to 100 V or 10 V to 140 V is employed.

Figure 2:
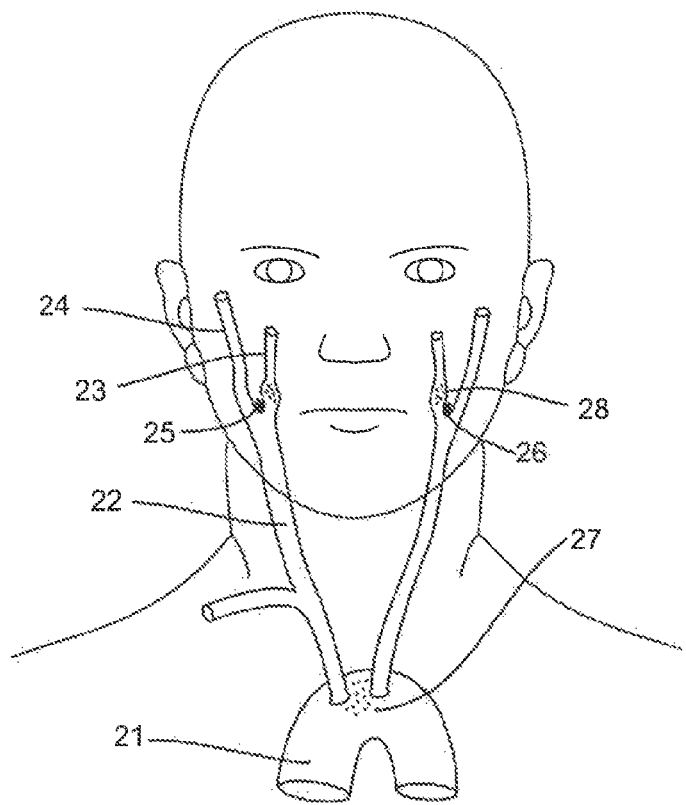
FIG. 2 is a representation of the carotid arteries showing the location of the carotid bodies.

FIG. 2 shows the location of arterial baroreceptors and the carotid bodies. The ascending aorta 21 feeds the carotid artery 22. Bifurcation of the internal carotid 23 and external carotid 14 forms a saddle in which the carotid bodies 25 & 26 are located. The aortic arch baroreceptors 27 feed the vagus nerve which is routed to the medulla. The carotid baroreceptors 28 are located on the internal carotid artery 23. Both the carotid bodies and carotid baroreceptors feed the sinus nerve of Herring which joins the glossopharyngeal nerve before reaching the medulla.

Figure 3:
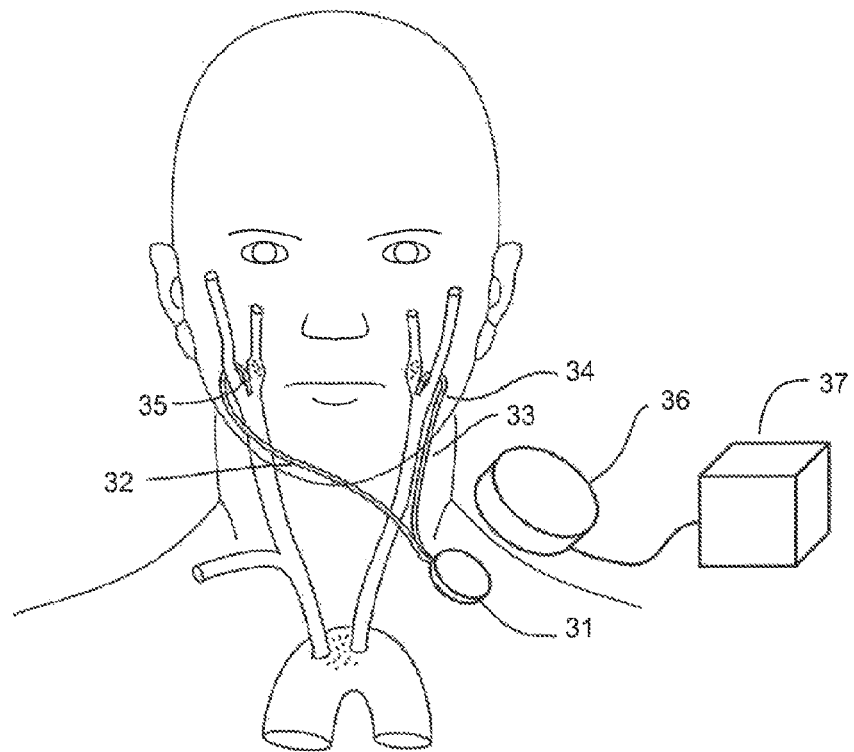
FIG. 3 is an example of an inductively coupled pulsed RF device implanted in the body with two outputs to drive two independent electrodes each implanted over the carotid bodies.

FIG. 3 shows a typical implantation of an inductively coupled RF device according to this invention. A receiving coil and electronics module 31 is implanted typically 5 to 10 mm and preferably less than 20 mm under the skin, which is connected to two flexible wires 32 & 33, each containing two cores of insulated biocompatible wire. Each wire terminates with two electrodes 34 & 35 which are implanted over the target of interest, the carotid bodies. An external transmitting coil 36 is connected to an external generator 37 supplying RF energy via magnetic induction to the implanted coil.

Figure 4:
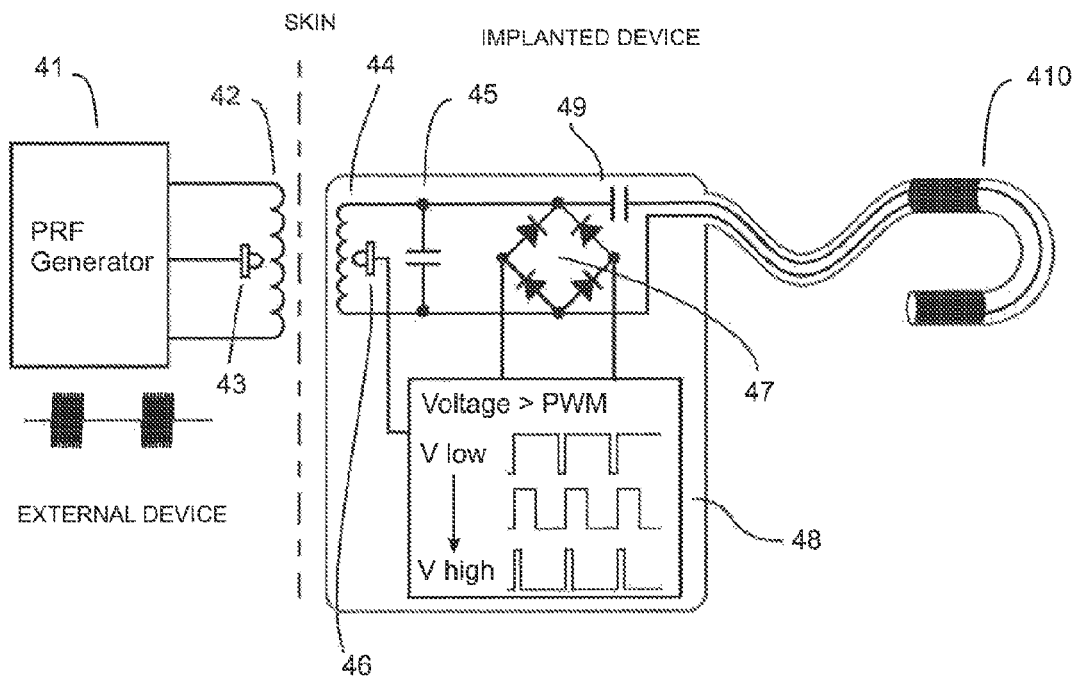
FIG. 4 is a block diagram of an inductively coupled pulsed RF device, showing major functional elements.

FIG. 4 is a block diagram of an inductively coupled pulsed RF device according to this invention illustrating the means of controlling output voltage at the required set-point. The external generator 41 drives an external coil 42 which has an infrared sensor 45 built into the centre of the coil. The implanted device has a receiving coil 44 which is tuned to be resonant with a parallel capacitor 45. As previously described, two factors with this arrangement that must be optimised are:

1. Adjusting the frequency of the RF output from the external generator to compensate for component tolerances and tissue capacitance, both which will shift the resonance frequency of the implanted coil.

2. Controlling the output voltage to the electrodes 410 to a predefined set-point amplitude so that heating does not occur.

In order to facilitate this, the output from the receiving coil is first rectified by a bridge rectifier 47. A full bridge rectifier is preferred as it loads the AC output from the coil equally, thereby reducing any DC offset, which is undesirable as this results in transport of ionic species away from the electrodes into the tissues leading to long term electrode decomposition and possible toxicity. Any residual imbalance may be compensated by the series capacitor 49, although this is optional provided that a balanced means of extracting energy from the coil is employed. It will be appreciated by those skilled in the art that other configurations are possible, for example a centre tapping on the receiving coil 44 to provide a zero voltage reference might simplify the design of the power supply for the sensing and LED drive block labelled Voltage>PWM 48. The Voltage>PWM circuit generates a pulse width modulated (PWM) current controlled drive to the implanted infrared light emitting diode (LED) 46. Preferably, the PWM mark-space ratio is inversely proportional to the average voltage output from the receiving coil as this reduces the dissipation of the current source for the LED when operating at high voltage.

The block diagram shows only a single output channel, but in practice two or more channels may be implemented, in particular two channels are ideal for targeting the left and right carotid bodies. It is also preferable that each channel has galvanic isolation from the other channel(s) to eliminate cross currents between distant electrodes. This may be achieved by using isolation transformers or by winding a receiving coil with the appropriate number of independent windings. Provided the independent windings are interlaced, it is only necessary to provide voltage feedback from a single channel.

Figure 5:
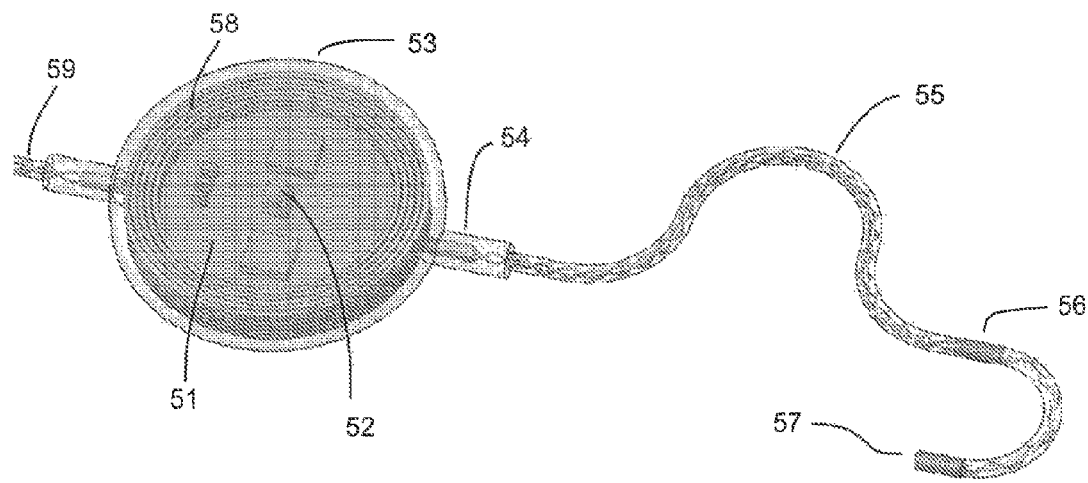
FIG. 5 is a drawing of a typical embodiment of an inductively coupled implantable RF device, showing one implantable lead (typically two will be provided).

FIG. 5 shows one implementation of the implantable receiving device and implantable lead according to this invention. The device consists of a receiving coil 58, printed circuit board 51, infrared LED 52, lead connector 54 and enclosure 53. A non-conducting enclosure is required to minimise eddy current losses in view of the high peak power transferred. If hermetic sealing is deemed important the enclosure is therefore constructed of a ceramic material, or if hermetic sealing is not important the enclosure may be constructed from biocompatible grades of silicone. Silicone is simpler and cheaper to implement than ceramic, is permeable to water molecules but not ionic carriers. The selection of enclosure is determined by cost and regulatory constraints, in general silicone in acceptable in Europe but not in the USA. Additional protection of the implanted circuit by means of conformal coating prior to encapsulation is preferable, but with a silicone enclosure careful attention to bonding of the silicone encapsulation to the circuit and coil is important to prevent long term failure, so conformal coatings that adhere well to silicone are essential. The lead wire 55, and second lead wire 59 (only partially shown but identical) is a flexible lead with twisted cores so that it can tolerate implantation in the neck, which is a highly mobile region. The wires are typically multi stranded platinum 10% iridium or MP35N with a silver core, trademarked as DFT wire. A variety of biocompatible insulators may be employed, such as polyimide, silicone or a combination thereof. Silicone encapsulation is preferred as the material is available in grades that are very flexible, thereby allowing the lead to stretch to accommodate movement and reduce the risk of electrode migration. At the distal end two electrodes 56 & 55 provide tissue contact. These electrodes are typically Pt-10Ir or Pt-20Ir for biocompatibility. The wire shown in the drawing has been shortened for clarity, the coil will typically be implanted under the clavicle and the wires tunneled up the neck in the subcutaneous tissues. An alternative electrode arrangement, not shown, is to have a single electrode at the distal end of the lead, with the return path provided by a return electrode on the enclosure or nearby to the implantable receiving device.

Figure 6:
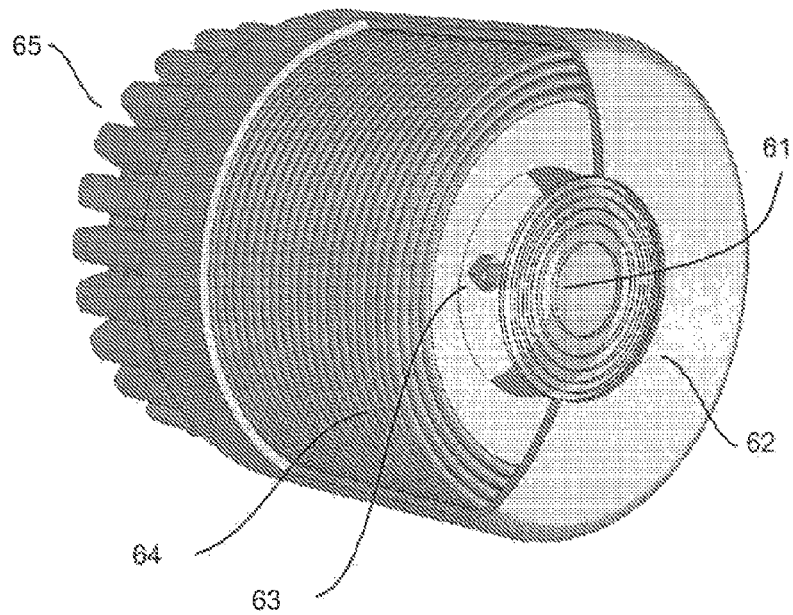
FIG. 6 is a drawing of a typical embodiment of the external transmitting coil for the RF device in figure five.

FIG. 6 shows an implementation of an external transmitting coil, with a partial section so that the inner components of the device are visible. The coil 64 is typically three times the diameter of the internal receiving coil and of approximately equal length and diameter. Treatment typically lasts a few minutes, during which the coil may be energised with peak power of 100 W to 1 kW, although average power is somewhat lower as the pulse duty cycle is typically 10% or less. In order to protect the patient from heat, a plastic enclosure 62 is preferable with the coil wound on a ceramic heat-sink 65 if required. The transmitting coil also contains an infrared lens, typically a Fresnel lens, to collect light from the implanted infrared LED, which is focused on an infrared receiver, 63.

Figure 7:
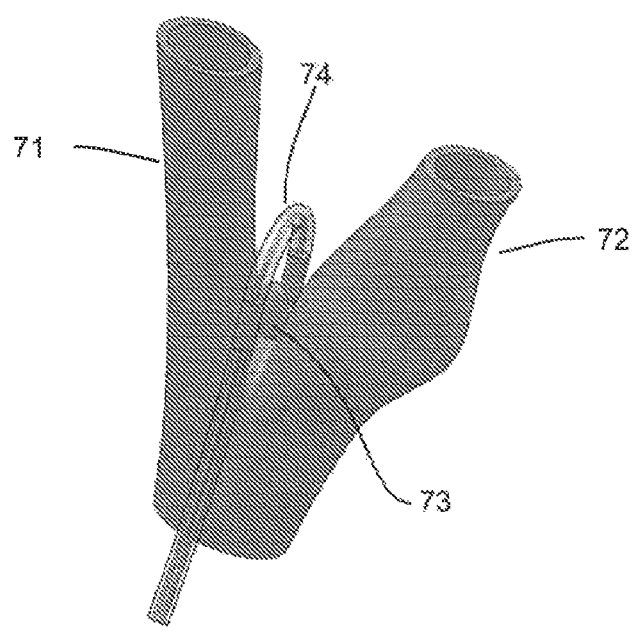
FIG. 7 is an illustration of the placement of the electrode from the device in figure five positioned over the left carotid body.

FIG. 7 illustrates placement of the distal end of the implanted lead, 74, in the bifurcation between the internal 72 and external carotid artery 71, over the carotid body 73. This is an idealised view; the carotid body is a small target approximately the size of a grain of rice in humans and may be buried in the artery wall. The semicircular shape of the end of the lead prevents migration and ensures that the electrodes are positioned either side of the carotid body, maximising the electric field potential of the applied RF signal in the region of the target.

Figure 8:
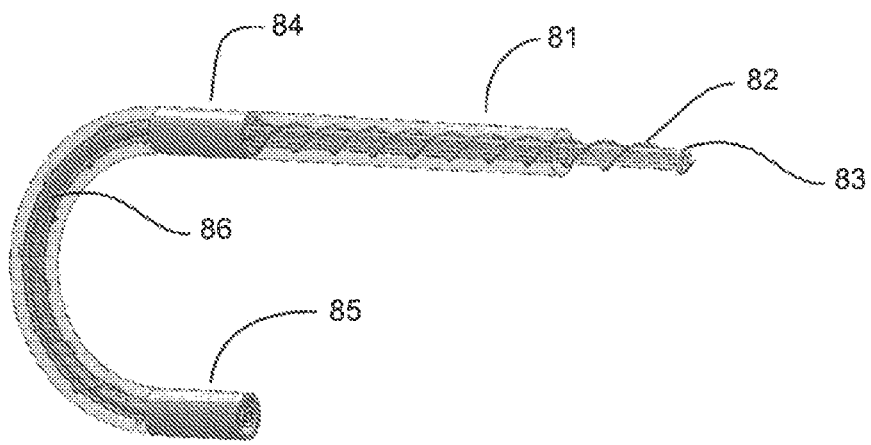
FIG. 8 is a detail of the distal end of the implantable lead.
Figure 9:
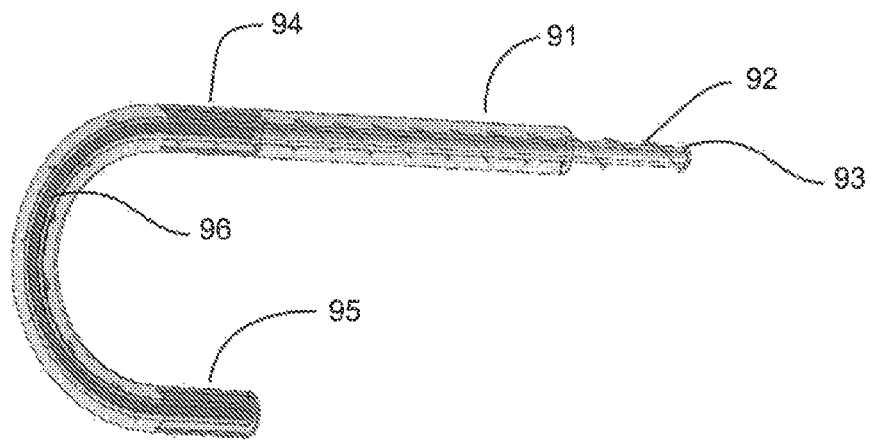
FIG. 9 is a cross section of figure eight.

FIG. 8 is a detail of the distal end of the lead and FIG. 9 is the same view in section. The lead comprises an internal guide tube, 83 & 93, which has a central hole of approximately 0.4 mm diameter to accept a guide wire, not shown. In order that the lead is flexible and extensible, the conductors, 82 & 92, are wound in a spiral around the guide tube prior to encapsulation in the outer sheath 81 & 91. The guide tube and outer sheath are preferably manufactured from biocompatible silicone as this is an elastic material. A first electrode 84 & 94 is connected to one conductor is separated by a semicircular section of the lead from a second electrode, 85 & 95. The semicircular section is preferably formed by insertion of a curved semicircular spring, 86 & 96, in the central hole. The spring may be any suitable material, polymer or metal. The cobalt nickel molybdenum alloy Co-35Ni-20Cr-10Mo (MP35N) is particularly suitable for this purpose.

Figure 10:
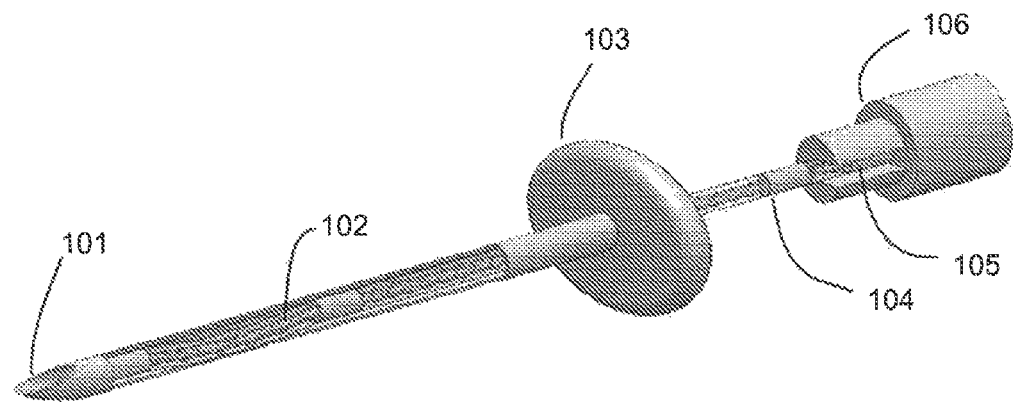
FIG. 10 shows the implantable lead installed in a tunneling needle used to introduce the lead into the vicinity of the carotid bodies.

FIG. 10 shows a device for introduction of the implantable lead, with the needle and lead shortened for clarity. A hollow Tuohy needle 101 with a displaced tip is shown partially sectioned. The implantable lead 102 is inserted into the needle, with the semi-circular section opened flat. The proximal end of the implantable lead has two contacts, 104 and 105 which form the connector for the implantable receiving device. A guide wire is inserted down the guide tube in the core of the lead extending the length of the lead up to the semi-circular spring; the guide wire incorporates a moulded handle 106 at the proximal end. Implantation of the lead using this device involves the steps described below:
1. A first incision is made in the upper part of the neck with exposure of the carotid bifurcation and a second incision is made in the lower part of the neck or upper chest at the site of the implantable receiving device.
2. A Tuohy needle is employed to tunnel from the second incision to the first incision. Preferably the Tuohy needle is supplied with the implantable lead already inserted for convenience.
3. Once the tip of the Tuohy needle is correctly positioned adjacent to the carotid bifurcation, the implantable lead is then pushed out of the needle using the guide wire so that the lead curves over the carotid bifurcation with electrode placement against the carotid body as illustrated in figure seven. The lead is then sutured in place.
4. The needle is withdrawn and connected to the implantable receiving device, which is inserted in a subcutaneous pocket with the face of the implant preferably less than 10 mm below the surface of the skin.

The method is repeated for the contra lateral carotid, although unilateral placement for effect may be sufficient.

An alternative to the above method involves the steps as follows:
1. A first incision is made in the upper part of the neck with exposure of the carotid bifurcation and a second incision is made in the lower part of the neck or upper chest at the site of the implantable receiving device.
2. A tunneling device such as a Trocar inside a plastic cannula (guide tube) is employed to tunnel from the first incision to the second incision, or vice-versa.
3. The Trocar is withdrawn leaving the cannula in place.
4. The implantable lead is introduced into the cannula, either from the site of the first incision or the second incision, with the curved part of the implantable lead overlying the carotid bifurcation as illustrated in figure seven and then sutured in place.
5. The cannula is withdrawn and the implantable lead is connected to the implantable receiving device, which is inserted in a subcutaneous pocket with the face of the implant preferably less than 10 mm below the surface of the skin.

Figure 11:
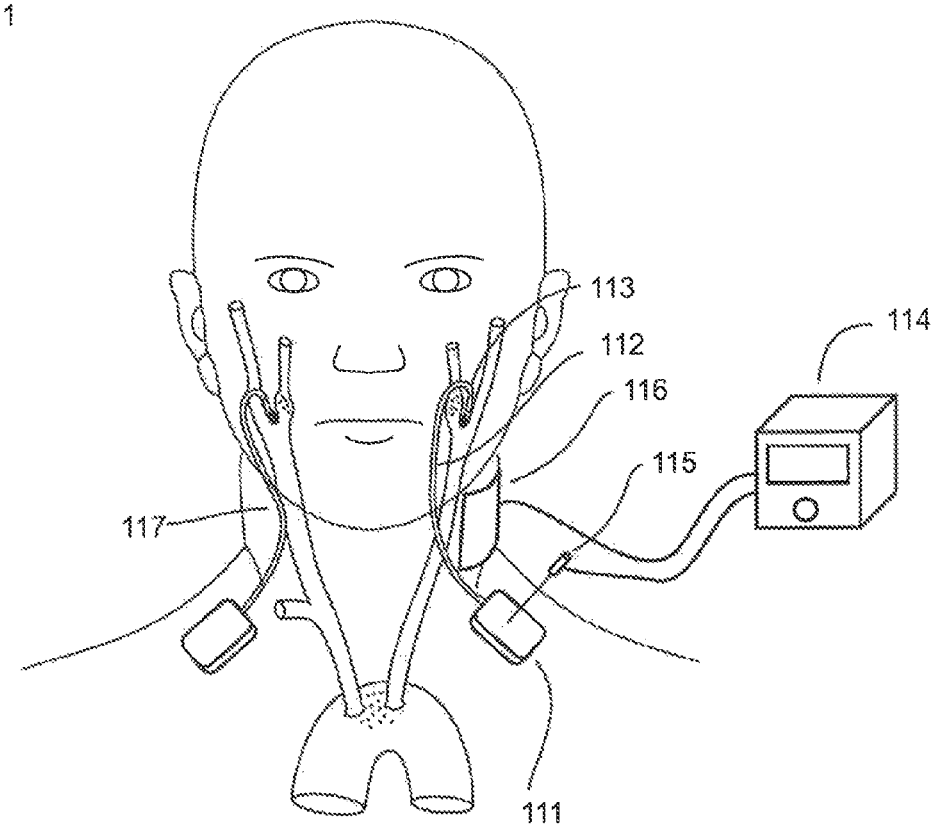
FIG. 11 is an example of a directly coupled pulsed RF device implanted in the body with independent electrodes each implanted over the carotid bodies.

FIG. 11 shows a typical implantation of a directly coupled RF device according to this invention. The internal contact 111 is implanted typically 10 mm under the skin and is connected to an insulated biocompatible single core wire 112 which terminates with an electrode 113 implanted over a carotid body. RF energy is supplied from the external generator 114 via a percutaneous needle 115 with the return path provided by an external skin electrode 116. In the example illustrated, a second implantable contact, wire and electrode 117 are used to target the other carotid body. An alternative to this is to connect both left and right electrodes to the same implantable contact. In this case, the method comprises applying RF energy with the skin electrode 113 positioned on the skin directly over one carotid body, then repeating the treatment with the skin electrode positioned over the contra lateral carotid body in order to ensure that RF energy is delivered to both carotid bodies.

FIG. 12 shows a block diagram of a directly coupled RF device. The external generator 121 is connected to a needle 122 which is introduced percutaneously to make contact with the implantable port 123. An insulated lead 124 routes the electrical energy to the electrode at the distal end of the lead 127. The return path is provided by a surface electrode 124, which is typically a self adhesive electrode of the type employed for transcutaneous nerve stimulation, preferably with a silver or stainless steel conductor within the pad rather than the cheaper carbon pads in order to carry the high peak current associated with pulsed RF waveforms which may reach one amp or more peak.

FIG. 13 provides detail of the construction of the implantable components. The implantable port consists of a wire mesh 131 with backing plate 132. The mesh comprises multiple layers, typically four to eight layers, formed by folding a strip of material in a concertina fashion so that all layers are electrically connected to produce a contact that is typically 15 to 25 mm square. The contact is encased in a silicone enclosure 133, but not bonded to the enclosure so the wires in each layer are free to move to accommodate the tip of the percutaneous needle 134. The mesh may be made of any biocompatible conductive material, such as stainless steel, typically comprising a mesh of 0.1 mm diameter wires spaced 0.25 mm apart. A percutaneous needle of 0.2 mm diameter is suitable for this configuration. The needle diameter is similar to acupuncture needles, so it can be introduced percutaneously without the use of local aesthetic. An advantage of the mesh contact compared to prior art devices is that it allows for greater error in alignment of the needle with respect to the port. As long as the needle penetrates somewhere in the area of the contact electrical continuity is assured. Further advantages are that it accommodates a small diameter needle and is low profile. The lead wire 135 is preferably detachable from the implantable port and contains an internal hole to accept a guide wire and semicircular distal end 136 with internal spring as previously described.

Figure 14:
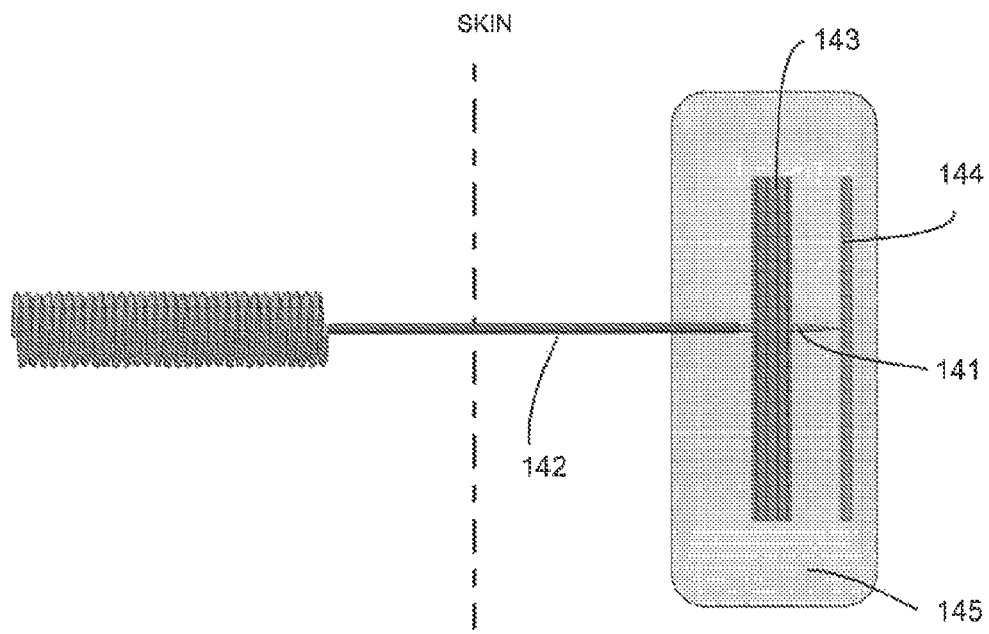
FIG. 14 is a side view in detail of the device illustrated in figure thirteen.

FIG. 14 is a side view of the implantable port and needle showing the exposed tip of the needle 141 penetrating the mesh 143. The backing plate 141 is a solid thin sheet of material, preferably also conductive and electrically connected to the mesh. The enclosure 145 is a low modulus biocompatible silicone material so that it allows the needle to penetrate and seals against the insulated shaft 142 of the needle, preventing local electrical connection with the tissues. As previously described, the mesh is not bonded to the silicone to allow the wires to move freely, but a layer of silicone between the mesh and backing plate is provided to stabilise the needle so that movement does not cause changes in contact resistance. The arrangement as described in capable of carrying 2 A peak currents at 500 kHz with no appreciable heat generation in the contact. Contact resistance is typically 3 ohms or less. It will be appreciated that the implantable port as described is not necessarily limited to carrying RF waveforms, but can also be used to deliver pulses of any duration, for example 50 to 200 ms pulses for nerve stimulation.

Figure 15:
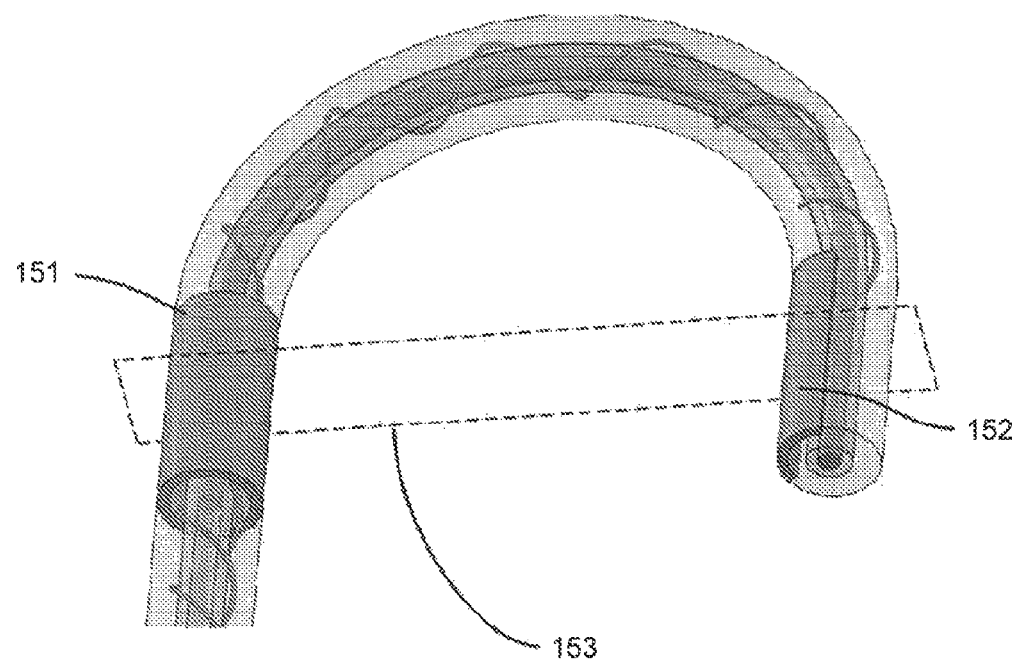
FIG. 15 is a diagram of an alternative arrangement of the distal end of the implantable lead.

FIGS. 15 and 16 illustrates an alternative arrangement of the implantable lead. As previously described, it is preferable that the energy from the implantable electrodes is directed towards the carotid body rather than other nearby structures. For example, suppression of output from baroreceptors on the carotid sinus would tend to cause an increase in arterial pressure. Figure fifteen shows the distal end of the implantable lead according to this alternative arrangement in which the proximal electrode 151 (if present) is of cylindrical form as before, but the distal electrode 152 is a segmented so that only the tissues closest to the carotid body are in electrical contact. In practice, this segmented arrangement can be achieved by either forming the electrode as a physical segment as illustrated, or by employing a cylindrical electrode and insulating the sector which is not required by means of a thin layer of insulating material such as silicone. This second option is preferred as it is more robust.

FIG. 16 is a schematic representation of a section of the carotid with the implantable lead in position at the level indicated by the plane 153 in figure fifteen, just above the bifurcation of the internal carotid 161 and external carotid 162. The carotid sheath 163 is connective tissue that surrounds the carotid arteries and the internal jugular vein 164. The carotid body 165 is displaced towards the external carotid whereas baroreceptors are located mainly on the carotid sinus at the origin of the internal carotid. The sympathetic chain ganglia 168 runs behind the carotid sheath in relatively close proximity. The proximal electrode 166 is of cylindrical form whereas the distal electrode 167 is comprised of a segment which overlies and is aligned towards the carotid body so that RF energy from the electrode is directed towards the carotid body and away from nearby baroreceptors and the sympathetic chain ganglia. Such an arrangement provides the dual benefit of enhancing the efficiency of therapy delivery and reducing potential side effects. Efficiency of therapy delivery in important as it allows a more compact implantable receiving device with the additional benefit that it may be possible to implant the device locally in the neck with a single incision.

The invention claimed is:

1. A device for treatment of hypertension, asthma, or chronic obstructive pulmonary disease, arranged to supply electrical energy to the carotid body or bodies in the form of a pulsed radio frequency waveform, having a frequency of 200 to 600 kHz comprising:
   an external generator;
   an implantable receiving device arranged to receive electrical energy from the external generator;
   at least one implantable lead connected to the implantable receiving device, the at least one implantable lead being adapted to deliver electrical energy to the carotid body or bodies by means of one or more electrodes at its distal end; and wherein
   the carotid body or bodies are located in a saddle of a bifurcation of an internal and an external carotid.

2. The device of claim 1, wherein the distal end of the at least one implantable lead incorporates a semi-circular hook, in which the semi-circular hook incorporates said one or more electrodes.

3. The device of claim 2, wherein at least one electrode is connected by an insulated wire of the least one implantable lead to the implantable receiving device such that the at least one electrode can be held in close proximity to the carotid body, such that the electrical energy supplied to the carotid body by the at least one electrode has an electrical return path provided by another electrode of said treatment device.

4. The device of claim 2, wherein two electrodes form said one or more electrodes, and the two electrodes are present on each side of the semi-circular hook and are connected by insulated wires of the implantable lead to the implantable receiving device such that the electrodes are positioned on each side of the carotid bifurcation.

5. The device of claim 2, wherein the semi-circular hook allows the at least one implantable lead to be adapted to sit over the bifurcation of the internal and external carotid.

6. The device of claim 5, wherein the semi-circular shaped hook is formed by a spring so that the hook can be flexible to allow insertion via a tunneling tool.

7. The device of claim 6, wherein the tunneling tool is one of a hollow hypodermic needle or a guide tube.

8. The device of claim 1, wherein the implantable receiving device is inductively coupled to the external generator.

9. The device of claim 8, wherein the implantable receiving device comprises:
   a near-infrared light emitting diode for feedback of the voltage at a receiving coil; and
   an external transmitting coil that has an infrared photo detector on its surface configured to detect the activation of the implanted near-infrared light emitting diode.

10. The device of claim 9, wherein the implantable receiving device is arranged to detect the resonance frequency of the receiving coil using the feedback from the near-infrared light emitting diode, and to thereby control the voltage delivered to the electrode of the at least one implantable lead.

11. The device of claim 1, wherein the implantable receiving device is directly coupled to the external generator.

12. The device of claim 11, wherein the implantable receiving device incorporates an implantable port comprising a contact of conductive wire mesh enclosed in a low modulus silicone outer case, and a percutaneous needle with insulated shaft with an exposed tip which is inserted into the implantable port to make electrical contact and connected to the external generator.

13. The device of claim 2, wherein the semi-circular hook is made from an elastic material.

14. The device of claim 1, wherein the device does not include a temperature sensor.

15. The device of claim 10, wherein the implantable receiving device further comprises a capacitor connected electrically in parallel to the receiving coil, said capacitor having a resonant frequency of 250-500 kHz.

* * * * *